United States Patent [19]

Welcheck

[11] Patent Number: 5,300,028
[45] Date of Patent: Apr. 5, 1994

[54] METHOD AND APPARATUS FOR PREVENTING IMPROPER USE AND DISPOSAL OF HYPODERMIC NEEDLES

[76] Inventor: Jack S. Welcheck, R.D. 3, Conneautville, Pa. 16406

[21] Appl. No.: 779,133

[22] Filed: Oct. 17, 1991

Related U.S. Application Data

[63] Continuation of Ser. No. 685,274, Apr. 15, 1991, abandoned.

[51] Int. Cl.$^5$ ............................................. A61M 5/00
[52] U.S. Cl. ................................. 604/110; 604/192; 206/366
[58] Field of Search .............. 604/110, 187, 192, 263; 206/364, 365, 366

[56] References Cited

U.S. PATENT DOCUMENTS

| | | | |
|---|---|---|---|
| 3,073,307 | 1/1963 | Stevens | 604/192 |
| 3,114,455 | 12/1963 | Claisse et al. | 604/192 X |
| 4,485,918 | 12/1984 | Mayer | 604/263 X |
| 4,629,453 | 12/1986 | Cooper | 604/192 |
| 4,892,525 | 1/1990 | Herman, Jr. et al. | 604/192 X |
| 4,995,871 | 2/1991 | Sasaki et al. | 604/110 |

FOREIGN PATENT DOCUMENTS

| | | | |
|---|---|---|---|
| 3012646 | 10/1981 | Fed. Rep. of Germany | 604/110 |
| 2205043 | 11/1988 | United Kingdom | 604/110 |

*Primary Examiner*—John D. Yasko
*Attorney, Agent, or Firm*—Ralph Hammar

[57] ABSTRACT

A device for holding a sealed container for a sterile hypodermic needle while the seal is broken, the needle is coupled to a syringe and removed by the syringe from the container and used one or more times on a single patient and then returned by the syringe to the container and the syringe is disconnected from the needle. The container is then released to fall into a disposal means. This eliminates contamination of the needle and infection of doctors and other authorized personnel by handling of the needle.

8 Claims, 3 Drawing Sheets

METHOD AND APPARATUS FOR PREVENTING IMPROPER USE AND DISPOSAL OF HYPODERMIC NEEDLES

This application is a continuation of Ser. No. 07/685,274 filed Apr. 15, 1991, now abandoned.

Individual sterile hypodermic needles are available in evacuated sealed containers. This invention is intended to prevent improper use and disposal of such needles and to prevent infection of persons using the needles.

Figure 1B:
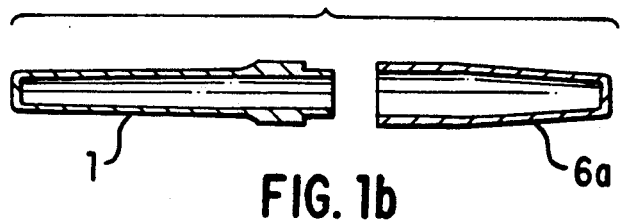
Figure 1A:
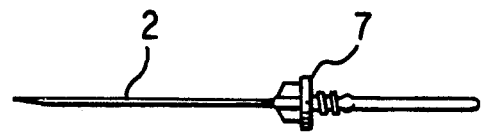
Figure 2:
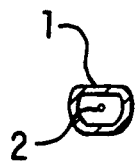
Figure 1:
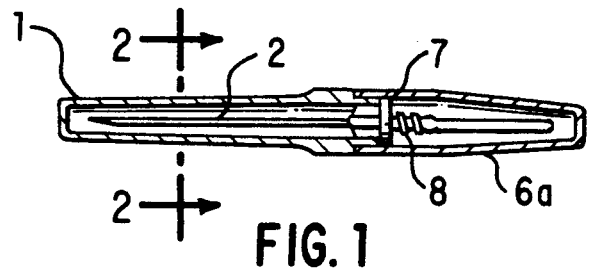
Figure 3:
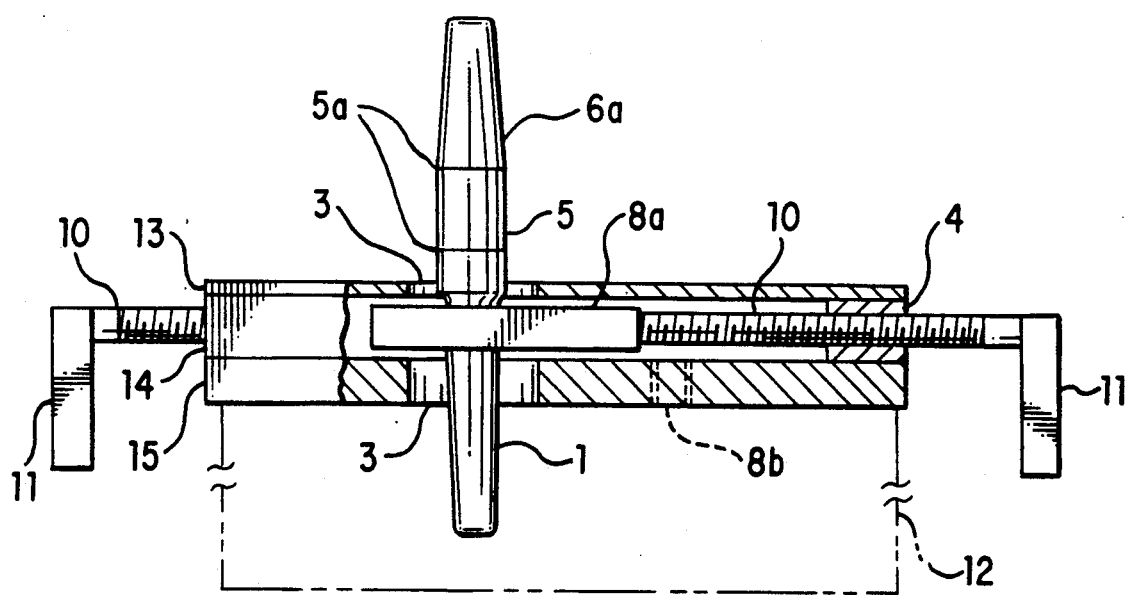
Figure 4:
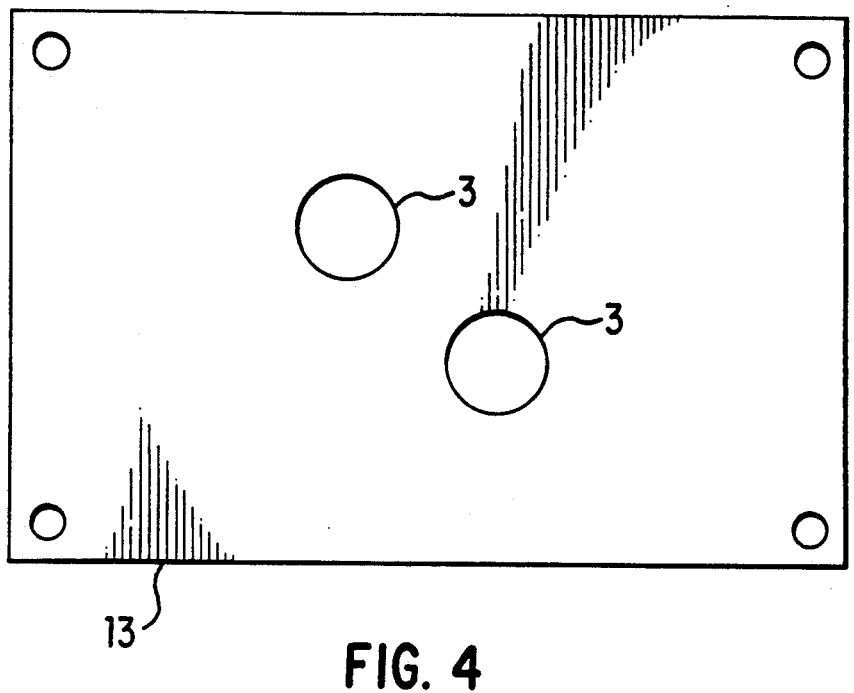
Figure 5:
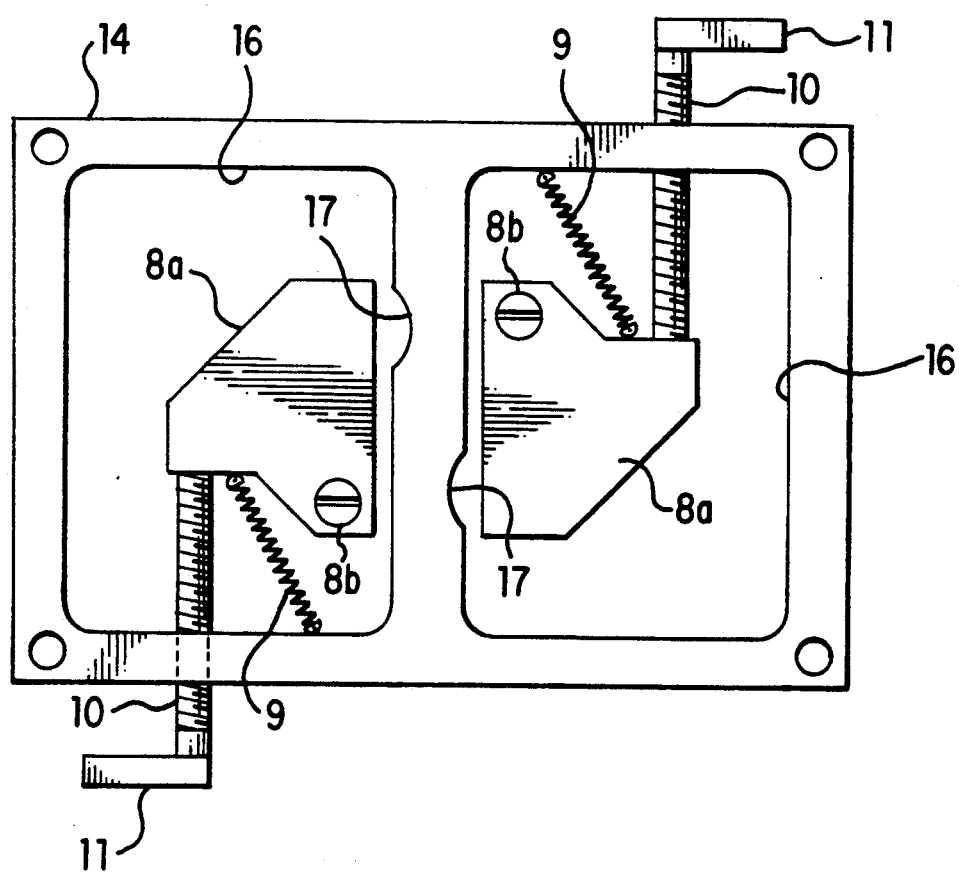
Figure 6:
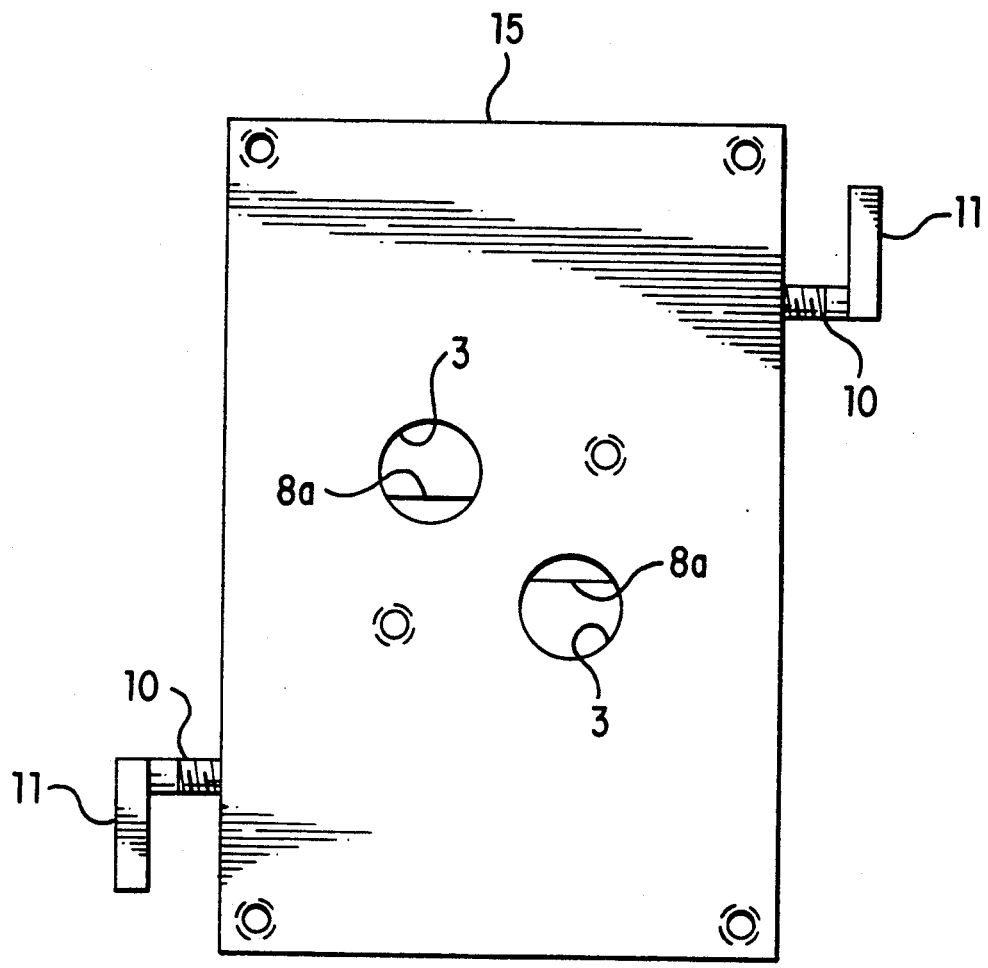

In the drawing, FIG. 1 is a sectional elevation of a sealed casing containing a sterile hypodermic needle, FIG. 1a is a view of the needle, FIG. 1b is a view of the parts of the casing or container, FIG. 2 is a section on line 2—2 of FIG. 1, FIG. 3 is a view showing the sealed casing fixed in an opening in a reusable disposal unit removably associated with a disposal container, FIG. 4 is top view of the disposal unit which may be mounted on or otherwise associated with a disposal container, FIGS. 5 and 6 are views of the parts of the disposal unit.

In a preferred form, a sealed evacuated casing or container 1 for an individual needle 2 is locked into one of the openings 3, in a disposal unit 4. As soon as the needle container is locked into the disposal unit, a seal 5 is broken by pulling tab 5a and cap 6a is removed to expose the hub 7 of the needle. A syringe (not shown) is then connected to coupling 8 on the needle hub. The needle 2 is then removed from its casing 1 by the syringe and is used one or more times on a single patient. Between uses, the needle and syringe may be parked in the needle casing. When no further use of the needle on that patient is required, the needle is returned; the syringe is disconnected from the needle to its casing 1 and disconnected from the after which the casing is released and allowed to fall into a removable disposal container 12. By this procedure, improper handling or use of the needle is prevented and infection of the user of the syringe is prevented.

The structure for locking the needle casing in the opening 3 in unit 4 comprises a lever 8a pivoted at 8b partly blocking the associated opening 3 and urged by tension spring 9 in a direction to enlarge or unblock the opening 3. The lever 8a is forced into gripping or locking position by screw 10 rotated by handle or lever 11.

When locked into the opening 3, the casing 1 cannot be rotated or moved up or down. After the hub 7 of the needle is connected to the syringe, the syringe may be used on a single patient for one or more injections. When use of the needle is no longer required by the single patient, the needle is returned by the syringe to its casing 1 and the syringe is disconnected from the needle. The screw 10 is then turned to release the gripping pressure on the casing 1 and the used needle and its casing drop into the disposal container 12 which is periodically disposed of in a safe manner. The unit 4 may then be mounted on a fresh disposal container 12 and used for another needle.

The reusable unit 4 comprises three plates 13, 14, 15. The top and bottom plates 13, 15 have concentric or registering openings 3. The center plate 14 has enlarged holes 16, each receiving a lever 8a cooperating with a semicircular recess 17 registering with the opening 3 against which casing 1 is clamped by a lever 8a.

There are a great many hermetically sealed sterile needles individually packaged. Also, there are a great many devices for disposing of used needles (Sharps). Difficulty has been experienced in inserting the used needles into the disposal device. The used needles (FIG. 14 of U.S. Pat. No. 4,995,871) are not friendly devices. The disposal units seem to involve inserting the needle point into a small opening.

The packages, of which Claisse et al. (U.S. Pat. No. 3,114,455) is an example, are user friendly. The packages are easy to handle. There are no sharp points to be avoided. The openings through which needles are mounted in and removed from their packages are also user friendly.

Applicant avoids all of the dangers and difficulties of prior art needle disposal devices by inserting the sealed needle package in the disposal device and locking the package in place before the package is opened. This involves no possible danger to medical personnel. The opening of the package in applicant's device does not take place until after the needle package is locked into the needle disposal device.

After the needle package is locked in place, the seal of the package is broken and the needle hub is connected to the syringe. This operation involves no possible danger to medical personnel. The needle hub is far removed from the needle point.

After the needle hub is connected to the syringe, and only then, the needle is removed from its package by the syringe and used for one or more injections on a single patient. Between injections, if desired, the needle may be returned by the syringe to its package and the syringe and needle parked there awaiting further use on the same patient, e.g., a supplemental injection. When there is no further need for the needle, the needle is returned by the syringe to the package and the syringe is disconnected from the needle hub. Then, and only then, is the package released and allowed to fall into the disposal container.

We have gone through the sequence of operations with applicant's structure to show that at all times applicant has avoided the danger of contact with needle points or sharps. Applicant's disposal unit is reusable with many, many disposable containers. Applicant's unit is independently sterilizable and is expected to be used for a long period of time, much like a machine tool in a factory.

The needle and the package the needle comes in are throw away items to be disposed of in a manner that does not endanger medical personnel or others. All of this is accomplished by applicant in a new fashion.

We claim:

1. A disposal unit having an opening, a casing received in said opening containing a sterile needle sealed in the casing by a seal,
   means for locking said casing in said opening while
   a) the seal is opened to expose the needle,
   b) a syringe is connected to the needle,
   c) the needle is removed by the syringe from the casing and used by the syringe one or more times on a single patient,
   d) the used needle is returned by the syringe to the casing,
   e) the syringe is disconnected from the needle,
   f) and then unlocking the casing and causing the casing and its needle to be delivered to disposal means.

2. The structure of claim 1 in which the disposal means is a removable disposal container.

3. The structure of claim 1 having a means for decreasing the size of said opening to grip the casing.

4. The structure of claim 1 in which the needle has a hub connected to the syringe.

5. The structure of claim 3 in which the opening is decreased in size by a lever movable toward one side of said opening.

6. The method of preventing infection by handling or using a sterile hypodermic needle individually packed in a sealed package which comprises locking the package in a convenient position and while the package is locked in position:
   a) opening the package to provide access to the needle hub,
   b) connecting a syringe to the needle hub,
   c) removing the syringe from the package by the syringe and using the needle on a single patient one or more times,
   d) returning the used needle to the package by the syringe,
   e) disconnecting the syringe from the used needle, and then
   f) unlocking the package and discharging the package and the needle contained therein to a disposal means.

7. The method of handling and disposing of an individual sterile needle packaged in a sealed container or casing which comprises:
   a) locking the sealed container in a disposal structure,
   b) opening the container to expose the needle hub,
   c) connecting a syringe to the needle hub,
   d) removing the needle by the syringe and using the needle one or more times on a single patient,
   e) returning the used needle by the syringe to its container and
   f) disconnecting the syringe from the needle hub, and then
   g) unlocking the container and causing the container and the used needle to be delivered to disposal means.

8. The method of claim 7 in which the disposal means is a removable disposal container.

* * * * *